US010736822B2

(12) United States Patent
Amao et al.

(10) Patent No.: US 10,736,822 B2
(45) Date of Patent: Aug. 11, 2020

(54) ROOT CANAL TREATMENT MATERIAL AND ROOT CANAL TREATMENT KIT

(71) Applicant: FUJIFILM Corporation, Tokyo (JP)

(72) Inventors: Akihito Amao, Ashigara-kami-gun (JP); Kumiko Yoshihara, Okayama (JP); Noriyuki Nagaoka, Kaga-gun (JP)

(73) Assignee: FUJIFILM Corporation, Tokyo (JP)

( * ) Notice: Subject to any disclaimer, the term of this patent is extended or adjusted under 35 U.S.C. 154(b) by 136 days.

(21) Appl. No.: 16/018,266

(22) Filed: Jun. 26, 2018

(65) Prior Publication Data

US 2018/0296445 A1 Oct. 18, 2018

Related U.S. Application Data

(63) Continuation of application No. PCT/JP2017/003131, filed on Jan. 30, 2017.

(30) Foreign Application Priority Data

Feb. 1, 2016 (JP) .................. 2016-017332

(51) Int. Cl.
| A61K 6/083 | (2006.01) |
| A61K 6/887 | (2020.01) |
| C08F 222/38 | (2006.01) |
| A61K 6/54 | (2020.01) |
| C08F 220/56 | (2006.01) |
| C08K 3/22 | (2006.01) |
| C08L 27/04 | (2006.01) |
| C09J 4/00 | (2006.01) |
| C08K 3/34 | (2006.01) |
| C08K 3/36 | (2006.01) |

(52) U.S. Cl.
CPC ............... *A61K 6/887* (2020.01); *A61K 6/54* (2020.01); *C08F 220/56* (2013.01); *C08F 222/385* (2013.01); *C08K 3/22* (2013.01); *C08L 27/04* (2013.01); *C08K 3/34* (2013.01); *C08K 3/36* (2013.01); *C08K 2003/2206* (2013.01); *C08K 2003/2244* (2013.01); *C09J 4/00* (2013.01)

(58) Field of Classification Search
CPC .................. A61K 6/083; A61K 6/887
See application file for complete search history.

(56) References Cited

U.S. PATENT DOCUMENTS

| 9,458,337 B2 * | 10/2016 | Yofu ...................... C08F 2/50 |
| 2002/0143138 A1 * | 10/2002 | Moszner .............. A61K 6/0017 528/310 |
| 2010/0081113 A1 | 4/2010 | Shinozaki et al. |
| 2011/0070563 A1 | 3/2011 | Ori et al. |
| 2011/0275675 A1 | 11/2011 | Rist et al. |
| 2014/0100390 A1 | 4/2014 | Amao et al. |

FOREIGN PATENT DOCUMENTS

| JP | 2002-212019 A | 7/2002 |
| JP | 2009-511615 A | 3/2009 |
| JP | 2010-083772 A | 4/2010 |
| JP | 2011-236211 A | 11/2011 |
| JP | 2012-206992 A | 10/2012 |
| JP | 2013-053075 A | 3/2013 |
| JP | 2014-118442 A | 6/2014 |
| JP | 2014118442 A | 6/2014 |
| JP | 2015-030796 A | 2/2015 |
| WO | 2007/045303 A1 | 4/2007 |
| WO | 2009/131250 A1 | 10/2009 |
| WO | WO2014050551 A1 * | 4/2014 |

OTHER PUBLICATIONS

International Preliminary Report on Patentability with a Translation of Written Opinion issued from the International Bureau in counterpart International Application No. PCT/JP2017/003131, dated Aug. 7, 2018.
Written Opinion dated Mar. 7, 2017, issued by the International Bureau in counterpart Application No. PCT/JP2017/003131.
International Search Report for PCT/JP2017/003131 dated Mar. 7, 2017 [PCT/ISA/210].
Notice of Reasons for Refusal dated Jun. 25, 2019 issued by the Japanese Patent Office in counterpart application No. 2017-565530.
Communication dated Jan. 18, 2019 from the European Patent Office in application No. 17747342.8.

* cited by examiner

*Primary Examiner* — Michael F Pepitone
(74) *Attorney, Agent, or Firm* — Sughrue Mion, PLLC

(57) ABSTRACT

The present invention provides a root canal treatment material having excellent curability in a moist environment and a root canal treatment kit containing the root canal treatment material. The root canal treatment material of the present invention includes: at least one compound (A) selected from the group consisting of a compound represented by Formula (1), a compound represented by Formula (2), and a compound represented by Formula (3); an acidic group-containing monomer (B); and a polymerization initiator (C).

10 Claims, No Drawings

ROOT CANAL TREATMENT MATERIAL AND ROOT CANAL TREATMENT KIT

CROSS-REFERENCE TO RELATED APPLICATIONS

This application is a Continuation of PCT International Application No. PCT/JP2017/003131 filed on Jan. 30, 2017, which claims priority under 35 U.S.C. § 119(a) to Japanese Patent Application No. 2016-017332 filed on Feb. 1, 2016. The above application is hereby expressly incorporated by reference, in its entirety, into the present application.

BACKGROUND OF THE INVENTION

1. Field of the Invention

The present invention relates to a root canal treatment material and a root canal treatment kit.

2. Description of the Related Art

In a case where tooth decay progresses up to the dental pulp and causes infection in the dental pulp, treatment is carried out by removing the tooth decay portion and exposing the dental pulp to remove the infected dental pulp. In this case, whether to remove the whole dental pulp or only the infected dental pulp is determined by a dentist based on the degree of inflammation, the age of a patient, the degree of completion of the dental root, or the like.

In addition to the tooth decay, treatment is necessary in a case where non-infectious exposure of the dental pulp accidentally occurs during formation of a cavity after removal of a tooth decay portion or occurs due to an external injury or in a case where the dental pulp is almost exposed while leaving a healthy dentin layer as a result of removing the carious dentin.

In the case as described above, treatment for preventing secondary infection is carried out by protecting the exposed (or almost exposed) dental pulp through coating the dental pulp or by protecting the root canal (cavity within the tooth generated by removing the dental pulp) after dental pulp extraction through filling. Such treatment of the dental pulp performed for the purpose of preserving a tooth function is called root canal treatment. At this time, a root canal treatment material called a pulp-capping material or root canal filling material is used for capping the exposed dental pulp or filling the root canal after the dental pulp extraction.

On the other hand, in recent years, various dental materials have been proposed. For example, JP2011-236211A discloses a dental material containing "at least one of a polymerizable ethylenically unsaturated monomer or an initiator for radical polymerization", an "organic and/or inorganic filler or filler mixture", "at least one monofunctional or polyfunctional (meth)acrylate or (meth)acrylamide or a mixture thereof", or a "mixture of an acidic monomer with a non-acidic monomer" in addition to a specific antibacterial active ingredient. In JP2011-236211A, it is disclosed that this dental material is used as a filling material for the dental root canal.

SUMMARY OF THE INVENTION

On the other hand, since the root canal treatment material is used in a humid environment in an oral cavity, it is necessary to proceed sufficient curing of the root canal treatment material even in such an environment.

The present inventors have applied the dental material disclosed in JP2011-236211A to the root canal treatment material, and as a result, they have found that the curability in a humid environment is insufficient and does not reach a level required as a root canal treatment material.

An object of the present invention is to provide a root canal treatment material having excellent curability in a humid environment from the viewpoint of the above-described circumstances.

Another object of the present invention is to provide a root canal treatment kit containing the above-described root canal treatment material.

The present inventors have conducted extensive studies on the above-described tasks, and as a result, they have found that it is possible to solve the above-described tasks using a root canal treatment material containing a (meth)acrylamide compound having a specific structure. More specifically, they have found that it is possible to solve the above-described tasks using the following configuration.

[1] A root canal treatment material comprising: at least one compound (A) selected from the group consisting of a compound represented by Formula (1), a compound represented by Formula (2), and a compound represented by Formula (3), all of which will be described below; an acidic group-containing monomer (B); and a polymerization initiator (C).

[2] The root canal treatment material according to [1], in which the compound (A) is at least one selected from the group consisting of a compound represented by Formula (1-1), a compound represented by Formula (2-1), a compound represented by Formula (2-2), and a compound represented by Formula (3-1), all of which will be described below.

[3] The root canal treatment material according to [1] or [2], in which the acidic group-containing monomer (B) contains a compound (B1) having at least one polymerizable group and acidic group in a molecule.

[4] The root canal treatment material according to [3], in which the polymerizable group is a (meth)acryloyl group, and the acidic group is at least one selected from the group consisting of a carboxyl group and a phosphoric acid group.

[5] The root canal treatment material according to any one of [1] to [4], further comprising: a filler (D).

[6] The root canal treatment material according to [5], in which the filler (D) is at least one selected from the group consisting of silica, zirconia, calcium silicate, and calcium hydroxide.

[7] A root canal treatment kit comprising: the root canal treatment material according to any one of [1] to [6].

According to the present invention, it is possible to provide a root canal treatment material having excellent curability in a moist environment. In addition, according to the present invention, it is possible to provide a root canal treatment kit containing the above-described root canal treatment material.

DESCRIPTION OF THE PREFERRED EMBODIMENTS

Hereinafter, a root canal treatment material and a root canal treatment kit of the present invention will be described.

In the present specification, the numerical range represented by "to" means a range including numerical values denoted before and after "to" as a lower limit value and an upper limit value.

In the present specification, (meth)acryl is a concept including both acryl and methacryl. Accordingly, for example, "(meth)acrylamide" is a concept including acrylamide and methacrylamide. That is, a (meth)acrylamide compound is a concept including an acrylamide compound and a methacrylamide compound. The (meth)acrylamide group is a concept including an acrylamide group ($CH_2$=CH—CO—NH—) and a methacrylamide group ($CH_2$=C($CH_3$)—CO—NH—). In addition, (meth)acrylate is a concept including acrylate and methacrylate, and (meth) acryloyl is a concept including acryloyl and methacryloyl.

The root canal treatment material of the present invention contains a compound (A), an acidic group-containing monomer (B), and a polymerization initiator (C), all of which will be described below.

Hereinafter, various components contained in the root canal treatment material of the present invention will be described in detail.

<Compound (A)>

The compound (A) is closely attached to the wall surface of the dental pulp or the root canal which is an adherend, and forms a part of a cured product through a polymerization reaction. The compound (A) has a function of preventing secondary infection of the dental pulp or the root canal after treatment of the root canal. The compound (A) is at least one compound selected from the group consisting of a compound represented by Formula (1), a compound represented by Formula (2), and a compound represented by Formula (3), and has two or more (meth)acrylamide groups in a molecule. For this reason, the compound (A) has a characteristic of excellent reactivity.

(Compound Represented by Formula (1))

The compound represented by Formula (1) contains four (meth)acrylamide groups and corresponds to a so-called polyfunctional (meth)acrylamide compound.

The compound represented by Formula (1) has an oxyalkylene group as a hydrophilic group and has an aspect in which a plurality of (meth)acrylamide groups are bonded through this group. Accordingly, a root canal treatment material more easily fits onto the wall surface of the dental pulp or the root canal which is an adherend in a moist environment, and the reactivity of the root canal treatment material becomes more superior.

An example of a suitable aspect of the compound represented by Formula (1) includes a compound represented by Formula (1-1) from the viewpoint of superior curability of the root canal treatment material in a moist environment (hereinafter, also simply referred to as a "viewpoint of a superior effect of the present invention").

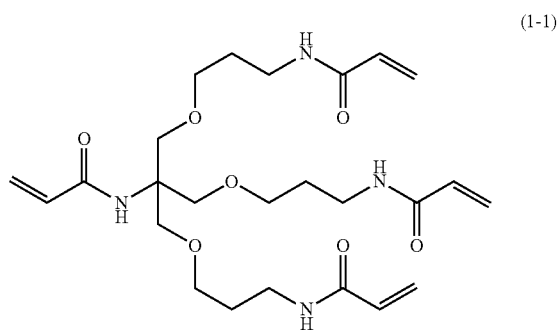 [SMILES: C=CC(=O)NCCCOCC(COCCCNC(=O)C=C)(COCCCNC(=O)C=C)NC(=O)C=C]
(1-1)

The compound represented by Formula (1-1) can be synthesized through a well-known method.

(Compound Represented by Formula (2))

The compound represented by Formula (2) contains three to five (meth)acrylamide groups and corresponds to a so-called polyfunctional (meth)acrylamide compound.

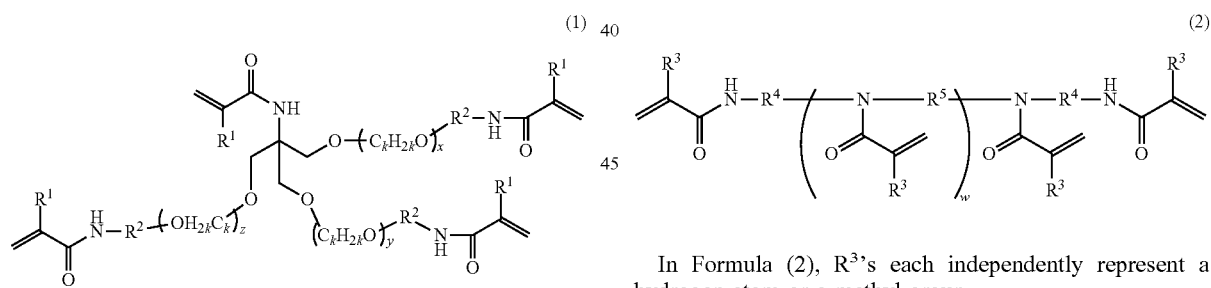

In Formula (1), $R^1$'s each independently represent a hydrogen atom or a methyl group.

$R^2$'s each independently represent a linear or branched alkylene group having 2 to 4 carbon atoms. However, in $R^2$, an oxygen atom and a nitrogen atom bonded to both ends of $R^2$ do not have a structure bonded to the same carbon atom of $R^2$.

k's each independently represent 2 or 3. A plurality of k's may be the same as or different from each other. In addition, the structure of $C_kH_{2k}$ may be a linear chain structure or a branched structure.

x, y, and z each independently represent an integer of 0 to 6, preferably an integer of 0 to 5, and more preferably an integer of 0 to 3. Although x+y+z satisfies 0 to 18, it preferably satisfies 0 to 15 and more preferably satisfies 0 to 9.

In Formula (2), $R^3$'s each independently represent a hydrogen atom or a methyl group.

$R^4$ and $R^5$ each independently represent an ethylene group or a 1,3-propylene group.

w represents an integer of 0 to 2.

Examples of suitable aspects of the compound represented by Formula (2) include a compound represented by Formula (2-1) and a compound represented by Formula (2-2) from the viewpoint of a superior effect of the present invention.

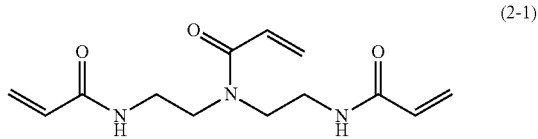
(2-1)

-continued

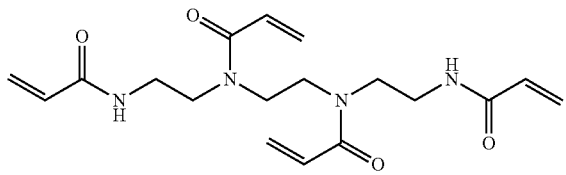

(2-2)

The compound represented by Formula (2-1) and the compound represented by Formula (2-2) can be synthesized through a well-known method.

From the viewpoint that a curable composition has superior curability, curability in a moist environment, and adhesiveness, the compound represented by Formula (2) is more preferably a compound represented by Formula (2-1).

(Compound Represented by Formula (3))

The compound represented by Formula (3) contains two (meth)acrylamide groups and corresponds to a so-called bifunctional (meth)acrylamide compound.

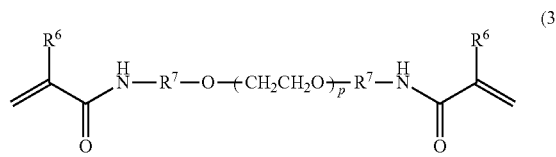

(3)

In Formula (3), $R^6$'s each independently represent a hydrogen atom or a methyl group.

$R^7$'s each independently represent an ethylene group, 1,2-propylene group, or a 1,3-propylene group.

p represents an integer of 0 to 6 and is preferably 0 to 2 from the viewpoint of obtaining a root canal treatment material having superior curability.

An example of a suitable aspect of the compound represented by Formula (3) includes a compound represented by Formula (3-1) from the viewpoint of a superior effect of the present invention.

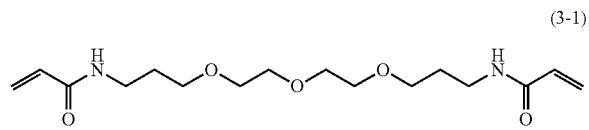 [SMILES: C=CC(=O)NCCCOCCOCCOCCCNC(=O)C=C]

(3-1)

The compound represented by Formula (3-1) can be synthesized through a method to be described below.

The compound (A) may be used alone, or in combination of two or more thereof.

The content of the compound (A) in the root canal treatment material with respect to the total solid content of the root canal treatment material is preferably 1 to 50 mass %, more preferably 3 to 30 mass %, and still more preferably 5 to 25 mass %. Sufficient curability in a moist environment can be obtained within the above-described numerical ranges.

In particular, the compound (A) is preferably the compound represented by Formula (1) from the viewpoint that the root canal treatment material has superior curability and curability in a moist environment.

The solid content of the root canal treatment material is a component that forms a cured product in a case of obtaining the cured product by subjecting the root canal treatment material to curing treatment, and corresponds to the above-described compound (A), an acidic group-containing monomer (B) to be described below, a polymerization initiator (C) to be described below, and the like. A solvent is not included in the solid content. In addition, even if a component thereof is a liquid, the component is calculated as a solid content as long as the component forms a cured product.

<Acidic Group-Containing Monomer (B)>

The acidic group-containing monomer (B) has a function of enhancing the adhesiveness of the root canal treatment material to the wall surface of the dental pulp or the root canal which is an adherend. The acidic group-containing monomer (B) contains a compound (B1) having at least one polymerizable group and acidic group in a molecule. The polymerizable group is preferably a radically polymerizable group, and examples thereof include a vinyl group, a vinyl cyanide group, and a (meth)acryloyl group. A (meth)acryloyl group is preferable from the viewpoint of excellent safety. Examples of the acidic group include a carboxyl group, a phosphoric acid group, a thiophosphoric acid group, a sulfonic acid group, and a sulfinic acid group, and a carboxyl group or a phosphoric acid group is preferable from the viewpoint of adhesiveness to the wall surface of the dental pulp or the root canal which is an adherend. In addition, an example of the acidic group includes an acidic group, such as an anhydride group of a carboxyl group, which becomes the above-described acidic group by being easily hydrolyzed under practical conditions and functions as a substantially acidic group. Two or more acidic groups and polymerizable groups may be present in a molecule.

In particular, in a case where the polymerizable group of the compound (B1) is a (meth)acryloyl group and the acidic group is at least one selected from the group consisting of a carboxyl group and a phosphoric acid group, the root canal treatment material has superior safety superior adhesiveness to an adherend.

Examples of the compound having a carboxyl group in the compound (B1) include α-unsaturated carboxylic acids such as (meth)acrylic acid and maleic acid; carboxylic acid compounds such as 11-(meth)acryloyloxy-1,1-undecane dicarboxylic acid in which a linear hydrocarbon group is present between a (meth)acryloyloxy group and a carboxyl group; (meth)acrylic acid compounds such as 6-(meth)acryloyloxyethylnaphthalene-1,2,6-tricarboxylic acid; (meth)acryloyloxyalkyl trimellitic acids such as 4-(meth)acryloyloxymethyl trimellitic acid, 4-(meth)acryloyloxyethyl trimellitic acid, and 4-(meth)acryloyloxybutyl trimellitic acid, or anhydrides thereof. Among these, 11-(meth)acryloyloxy-1,1-undecane dicarboxylic acid or 4-(meth)acryloyloxyethyl trimellitic acid is preferable and 4-(meth)acryloyloxyethyl trimellitic acid is more preferable from the viewpoint of superior adhesiveness to an adherend.

Examples of a compound having a phosphoric acid group in the compound (B1) include (meth)acryloyloxyalkyl acid phosphates such as 2-(meth)acryloyloxyethyl acid phosphate, 2-(meth)acryloyloxypropyl acid phosphate, 4-(meth)acryloyloxybutyl acid phosphate, 6-(meth)acryloyloxyhexyl acid phosphate, 8-(meth)acryloyloxyoctyl acid phosphate, 10-(meth)acryloyloxydecyl acid phosphate, 12-(meth)acryloyloxy dodecyl acid phosphate; acid phosphates, such as bis[2-(meth)acryloyloxyethyl] acid phosphate and bis[2- or 3-(meth)acryloyloxypropyl] acid phosphate, which have two or more (meth)acryloyloxyalkyl groups; acid phosphates, such as 2-(meth)acryloyloxyethyl phenyl acid phosphate and 2-(meth)acryloyloxyethyl-p-methoxyphenyl acid phosphate, which have a (meth)acryloyloxyalkyl group through an aromatic ring such as a phenylene group or a heteroatom such as an oxygen atom. Among these, 10-(meth)acryloyloxydecyl acid phosphate is preferable from the viewpoint of superior adhesiveness to an adherend.

The acidic group-containing monomer (B) may be used alone, or in combination of two or more thereof. The content of the acidic group-containing monomer (B) with respect to the total solid content of the root canal treatment material is preferably 5 to 20 mass % and more preferably 5 to 15 mass %. In a case where the content of the acidic group-containing monomer is within the above-described numerical ranges, adhesiveness to an adherend can be easily obtained sufficiently.

<Polymerization Initiator (C)>

A general polymerization initiator used for dental applications can be used as the polymerization initiator (C), and a photopolymerization initiator is preferable. Specific examples of the polymerization initiator (C) include organic peroxides, inorganic peroxides, diazo compounds, and organic boron compounds.

Examples of the organic peroxides include alkyl peroxides such as isobutyl peroxide and decanoyl peroxide; peroxycarboxylic acid anhydrides such as acetyl peroxide; aromatic peroxycarboxylic acid anhydrides such as benzoyl peroxide; peroxidic anhydrides of polycarboxylic acid such as succinic acid peroxide; peroxydicarbonates such as diisopropyl peroxydicarbonate, di-2-ethylhexyl peroxydicarbonate, diallyl peroxydicarbonate; ester peroxides such as tert-butyl peroxyisobutyrate, tert-butyl peroxyneodecanate, and cumene peroxyneodecanate; and peroxidic anhydrides of carboxylic acid and sulfonic acid such as acetyl cyclohexyl sulfonyl peroxide.

Examples of the inorganic peroxides include ammonium persulfate, potassium persulfate, potassium chlorate, potassium bromate, and potassium perphosphate.

Examples of the diazo compounds include 2,2'-azobisisobutyronitrile, 4,4'-azobis(4-cyanovaleric acid), 2,2'-azobis(4-methoxy-2,4-dimethoxyvaleronitrile), and 2,2'-azobis(2-cyclopropylpropionitrile).

Examples of the photopolymerization initiator include α-diketone compounds; camphorquinone compounds such as camphorquinone; naphthyl compounds such as α-naphthyl; benzyl compounds such as benzyl, p,p'-dimethoxybenzyl; B-diketone compounds such as pentadione; quinone compounds such as 1,4-phenanthrenequinone and naphthoquinone; benzoylphosphine oxide compounds such as diphenyl trimethyl benzoylphosphine oxide; and tertiary amine compounds.

The polymerization initiator (C) may be used alone, or in combination of two or more thereof.

The content of the polymerization initiator (C) with respect to the total solid content of the root canal treatment material is preferably 0.01 to 40 mass %, more preferably 0.05 to 35 mass %, and still more preferably 0.1 to 30 mass %. In a case where the content of the polymerization initiator is within the above-described numerical ranges, the polymerization rate is within a suitable range, the treatment time is sufficiently secured, and curing failure due to insufficient polymerization initiator hardly occurs.

<Other Components>

(Filler (D))

The root canal treatment material of the present invention may contain a filler (D). In the case where the root canal treatment material contains the filler (D), it is possible to obtain a root canal treatment material having superior mechanical strength and adhesiveness.

Examples of the filler (D) include an inorganic filler, an organic filler, or a composite filler thereof. Examples of the filler (D) include zinc oxide, pulverized quartz, wet silica, dry silica, carbon black, diatomaceous earth, glass fiber, alumina, magnesia, calcium carbonate, magnesium carbonate, hydroxyapatite, fluorinated apatite, titanium, zinc, zirconium, zirconia (zirconium dioxide), strontium, tin, barium, tungsten, bismuth, a pulverized polymer, and a powdered polymer.

A filler having a function of adjusting the pH to prevent secondary infection of the dental pulp or the root canal and a function of promoting hard tissue formation around an exposed dental pulp region is more preferable as the filler (D), and examples of such a filler include calcium hydroxide, mineral trioxide aggregate (MTA), and calcium silicate.

In addition, a filler containing a substance having X-ray impermeable X-ray contrasting properties is preferable as the filler (D), and examples of such a filler include lithium, barium, strontium, zirconium, and oxides thereof (for example, zirconia).

In addition, the inorganic filler may be subjected to surface treatment such as silane treatment or polymer coating.

Among these, the filler (D) is preferably at least one selected from the group consisting of silica, zirconia, calcium silicate, and calcium hydroxide in that the root canal treatment material has superior mechanical strength.

The filler (D) may not contain either calcium silicate or calcium hydroxide. In the case where the filler (D) does not substantially contain either calcium silicate or calcium hydroxide, it is impossible to obtain a root canal treatment material having superior adhesiveness to the wall surface of the dental pulp or the root canal which is an adherend. The expression "does not substantially contain" is intended that the content of calcium silicate and calcium hydroxide is less than or equal to 0.1 mass % with respect to the total mass of the filler (D). The content thereof is preferably less than or equal to 0.01 mass % and more preferably 0 mass %.

The filler (D) is preferably at least one selected from the group consisting of silica and zirconia in that the root canal treatment material has further superior mechanical strength and superior adhesiveness to an adherend.

Among these, silica is more preferable as the filler in that the root canal treatment material has superior bending strength.

The filler (D) may be used alone, or in combination of two or more thereof. The content of the filler (D) with respect to the total solid content of the root canal treatment material is preferably 10 to 90 mass %, more preferably 20 to 80 mass %, and still more preferably 30 to 80 mass %. In a case where the content of the filler is within the above-described numerical ranges, the strength of a cured product tends to be sufficient.

(Polymerizable Monomer)

The root canal treatment material of the present invention may contain a polymerizable monomer which does not have an acidic group but has at least one polymerizable group in a molecule for the purposes of improving the adhesiveness to the wall surface of the dental pulp or the root canal which is an adherend and improving water resistance of a cured product. As such a polymerizable monomer, for example, a monofunctional or polyfunctional (meth)acrylic acid ester is preferable from the viewpoint of safety and a bifunctional (meth)acrylic acid ester is more preferable from the viewpoint of obtaining a superior effect of the present invention.

Examples of the aliphatic monofunctional polymerizable monomer include methyl (meth)acrylate, ethyl (meth)acrylate, propyl (meth)acrylate, butyl (meth)acrylate, isobutyl (meth)acrylate, lauryl (meth)acrylate, and 2-hydroxyethyl (meth)acrylate (HEMA).

Examples of the aliphatic difunctional polymerizable monomer include erythritol di(meth)acrylate, sorbitol di(meth)acrylate, mannitol di(meth)acrylate, pentaerythritol di(meth)acrylate, dipentaerythritol di(meth)acrylate, glycerol di(meth)acrylate, ethylene glycol di(meth)acrylate (EGDMA), diethylene glycol di(meth)acrylate, triethylene glycol di(meth)acrylate (TEGDMA), polyethylene glycol di(meth)acrylate, propylene glycol di(meth)acrylate, butylene glycol di(meth)acrylate, and 2,2,4-trimethylhexamethylenebis (2-carbamoyloxyethyl) dimethacrylate (UDMA).

Examples of aliphatic tri- or higher-functional polymerizable monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol tri (meth)acrylate, dipentaerythritol tetra(meth)acrylate, and dipentaerythritol penta(meth)acrylate.

Examples of the aromatic monofunctional polymerizable monomer include benzyl (meth)acrylate, phenoxyethyl (meth)acrylate, and phenoxydiethylene glycol (meth)acrylate. An example of the aromatic difunctional polymerizable monomer includes 2,2-bis[4-[2-hydroxy-3-(methacryloyloxy) propyloxy] phenyl] propane (BisGMA).

The polymerizable monomer may contain a compound represented by Formula (4).

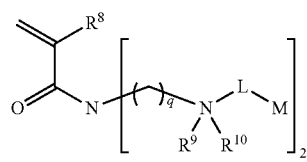

(4)

In Formula (4), $R^8$ represents a hydrogen atom or a methyl group, $R^9$ and $R^{10}$ each independently represent a methyl group, an ethyl group, an n-propyl group, or an i-propyl group, q represents an integer of 1 to 4, L represents a linear or branched alkylene group having 3 or 4 carbon atoms, and M represents $SO_3^-$ or $COO^-$.

The polymerizable monomer may be used alone, or in combination of two or more thereof. The content of the polymerizable monomer with respect to 100 parts by mass of the total solid content of the root canal treatment material is preferably 1 to 50 parts by mass, more preferably 3 to 30 parts by mass, and still more preferably 5 to 25 parts by mass, and particularly preferably 10 to 25 parts by mass. In a case where the content of the polymerizable monomer is within the range of 10 to 25 parts by mass with respect to 100 parts by mass of the total solid content of the root canal treatment material, superior bending strength is easily obtained.

(Antibacterial Agent)

The root canal treatment material of the present invention may contain an antibacterial agent for the purpose of preventing secondary infection of the dental pulp or the root canal. An inorganic antibacterial agent or an organic antibacterial agent can be used as the antibacterial agent.

Examples of the inorganic antibacterial agent include synthetic zeolite carrying inorganic ions such as silver ions, copper ions, and zinc ions; calcium phosphate carrying inorganic ions; vanadium phosphate carrying inorganic ions; calcium silicate carrying inorganic ions; silica gel carrying inorganic ions, zirconium phosphate carrying inorganic ions, an amorphous type carrying inorganic ions; titanium oxide carrying inorganic ions; and an oxide photocatalyst carrying inorganic ions.

Examples of the organic antibacterial agent include phenol ether derivatives, sulfone derivatives, imidazole derivatives, eugenol, and polymerizable monomers, such as (meth) acryloyloxy hexadecyl pyridinium bromide, (meth) acryloyloxy hexadecyl pyridinium chloride, and (meth) acryloyloxy decyl ammonium chloride, which have a cationic group.

The antibacterial agent may be used alone, or in combination of two or more thereof. The content of the antibacterial agent is preferably 0.1 to 10 parts by mass with respect to 100 parts by mass of the total solid content of the root canal treatment material. In a case where the content of the antibacterial agent is within the above-described numerical range, antibacterial properties appropriate for the blending amount are easily obtained.

(Colorant)

The root canal treatment material of the present invention may contain a colorant. Examples of the colorant include PHLOXINE BK, ACID RED, FAST ACID MAGENTA, PHLOXINE B, FAST GREEN FCF, RHODAMINE B, FUCHSINE BASIC, FUCHSINE ACID, EOSIN, ERYTHROSINE, SAFRANIN, ROSE BENGAL, BEMER, GENTIAN VIOLET, COPPER CHLOROPHYLL SODA, laccaic acid, sodium fluorescein, cochineal, shisonin, talc, and titanium white. The colorant may be used alone, or in combination of two or more thereof.

(Stabilizer)

The root canal treatment material of the present invention may contain a stabilizer. Examples of the stabilizer include hydroquinone compounds such as hydroquinone and dibutyl hydroquinone or phenols such as hydroquinone monomethyl ether, 2,6-di-tert-butylphenol, 2,6-di-tert-butyl, and 2,6-di-tert-butyl-p-cresol. The stabilizer may be used alone, or in combination of two or more thereof.

(Solvent)

The root canal treatment material of the present invention may contain a solvent for the purposes of improving solubility of constituent components, adjusting viscosity, and improving affinity with an adherend. Examples of the solvent include water and ethanol. The content of the solvent is preferably 1 to 50 parts by mass with respect to 100 parts by mass of the total solid content of the root canal treatment material.

The method for producing a root canal treatment material is not particularly limited, and a well-known method can be employed. Examples thereof include a method for mixing the above-mentioned components to produce a root canal treatment material and a method for adding the above-described various components to a predetermined solvent and dissolving the components, and then, removing the solvent as necessary to produce a root canal treatment material.

Next, a method of using a root canal treatment material of the present invention will be described.

The root canal treatment material of the present invention can be used in the same method as in a method in which conventional root canal treatment materials are used. Hereinafter, a general procedure of root canal treatment in a case where the root canal treatment material of the present invention is used as a pulp-capping material or a root canal filling material will be described. However, the method of using a root canal treatment material of the present invention is not limited by the procedure.

In case of using the root canal treatment material as a pulp-capping material, a moisture-proof rubber sheet called a rubber dam is first worn in the mouth of a patient, a hole is formed in the rubber dam in a portion of an affected tooth, and only the affected tooth is exposed from the rubber dam using a clamp. Thereafter, the carious dentin of the affected tooth is removed, the cavity is washed and sterilized with sodium hypochlorite solution and a hydrogen peroxide solution and further washed with a sterile physiological saline solution, and the cavity is dried with a sterile cotton ball. At this time, since the affected tooth is close to the dental pulp or the dental pulp is exposed, in some cases, drying of the cavity is insufficient due to leachate or the like. Thereafter, the root canal treatment material of the present invention is applied to the surface, on which the dental pulp is exposed, using a tool called an applicator. After curing the root canal treatment material through light irradiation, the root canal treatment material is relined with a lining material such as glass ionomer cement as necessary, and then, tooth crown restoration or the like is performed and the treatment is completed.

Even in a case where the root canal treatment material is used as a root canal filling material, the rubber dam is similarly worn in the mouth of a patient and the root canal in the affected tooth exposed from the rubber dam is washed with a sodium hypochlorite solution, a hydrogen peroxide solution, and the like. Then, the root canal is dried with a cotton plug broach or paper point. Even in this case, the drying may be insufficient for the same reason as described above. In addition, since the shape of the root canal differs depending on the patient, the part, and the individual tooth, in a case where the root canal is curved, in some cases, it is difficult to sufficiently dry the root canal. After drying the root canal, a root canal treatment material is applied to a needle-shaped rubber member called a gutta-percha point (main point) and the needle-shaped rubber member is inserted into a predetermined position of the root canal. Next, another gutta-percha point (accessory point) is inserted into a gap as necessary. Then, the main point is pressurized laterally with a tool called a spreader, the accessory point is further inserted into the formed gap, and this process is continued until the root canal is filled without any gap. Thereafter, tooth crown restoration or the like is performed and the treatment is completed. In addition to the above-described method, the root canal treatment material of the present invention can also be used for a method for directly filling the root canal with a root canal treatment material using an applicator or the like without using a gutta-percha, and curing the root canal treatment material.

As described above, in some cases, it is difficult to completely remove moisture from the wall surface of the dental pulp or the root canal which is an adherend in the root canal treatment. However, in a case of using the root canal treatment material of the present invention, the root canal treatment material firmly adheres to the wall surface of the dental pulp or the root canal even in a moist environment to form a stable cured product. Therefore, it is possible to seal the dental pulp or the root canal and it is possible to prevent the secondary infection of the dental pulp or the root canal after the root canal treatment.

<Root Canal Treatment Kit>

The root canal treatment kit containing the root canal treatment material of the present invention contains the root canal treatment material of the present invention and is composed of members required for other types of root canal treatment. In a case where the root canal treatment kit is used for, for example, filling the root canal, an example of the configuration of the root canal treatment kit includes a configuration in which consumable members such as a root canal filling material, gutta-percha, a detergent, and a paper point are combined. The root canal treatment kit of the present invention is not limited to the other members as long as it contains the root canal treatment material of the present invention, and it may be used for pulp-capping or for filling of the root canal.

EXAMPLES

Hereinafter, the present invention will be more specifically described with reference to examples. However, the present invention is not limited thereto. Unless otherwise specified, the units "parts" and "%" are on a mass basis.

<Synthesis of Compound (I)>

The compound (I) was synthesized according to the following scheme.

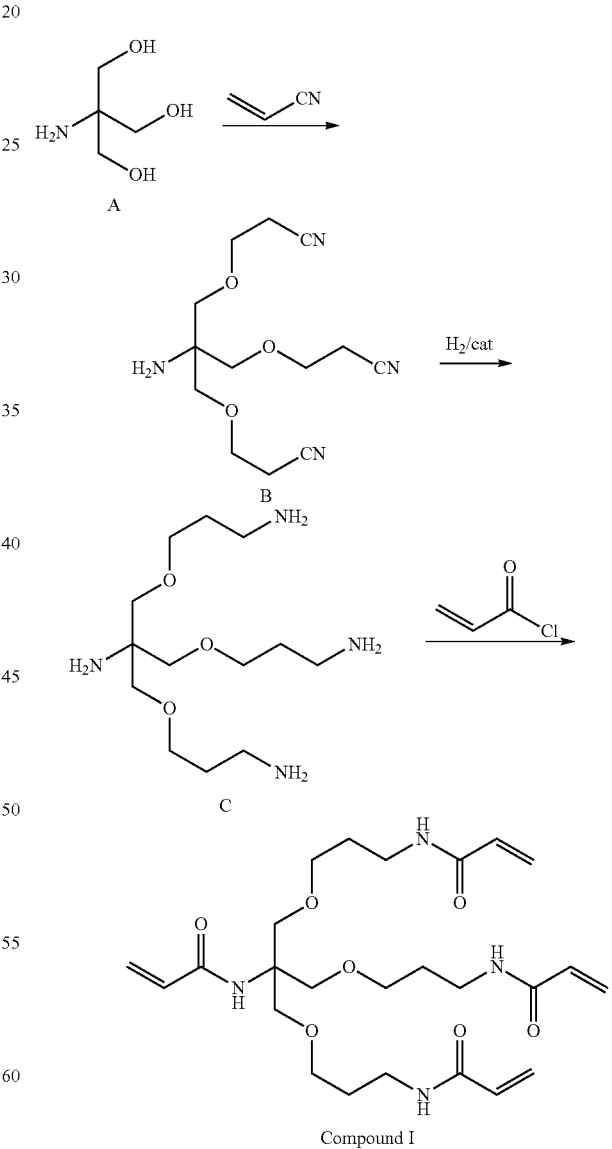

Compound I 121 g (1 equivalent) of tris(hydroxymethyl)aminomethane (A) (manufactured by Tokyo Chemical Industry Co., Ltd.), 84 mL of a 50% potassium hydroxide aqueous solution, and 423 mL of toluene were added to a 1 L three-neck flask equipped with a stirrer bar and the reaction solution was stirred. In a water bath, the temperature of the reaction solution was maintained at 20° C. to 25° C. and 397.5 g (7.5 equivalents) of acrylonitrile was added dropwise to the reaction solution over 2 hours to obtain a reaction solution. Next, the reaction solution was stirred for 1.5 hours. Next, 540 mL of toluene was added to the reaction solution to obtain a reaction mixture. Next, the above-described reaction mixture was transferred to a separatory funnel and the aqueous phase was removed to obtain an organic phase. Next, the organic phase was dried with magnesium sulfate and was subjected to celite filtration, and the solvent was distilled off under reduced pressure to obtain an intermediate (B). Next, the intermediate (B) (24 g), 48 g of an Ni catalyst (RANEY NICKEL 2400 manufactured by W.R. Grace & Co.), and 600 mL of a solution of 25% ammonia water: methanol=1:1 were placed in a 1 L autoclave (hereinafter, also referred to as a "reaction container") and suspended, and the reaction container was sealed. Next, hydrogen at 10 MPa was introduced into the reaction container and reacted at a reaction temperature of 25° C. for 16 hours to obtain a reaction solution.

Next, disappearance of a signal derived from the raw materials in the reaction solution was checked through $^1$H-NMR (nuclear magnetic resonance), the reaction solution was subjected to celite filtration, and the celite was washed several times with methanol to obtain a filtrate. Next, the solvent was distilled off from the obtained filtrate under reduced pressure to obtain an intermediate (C).

Next, 30 g of the intermediate (C), 120 g (14 equivalents) of NaHCO$_3$, 1 L of dichloromethane, and 50 mL of water were added to a 2 L three-necked flask equipped with a stirrer to obtain a reaction solution. Next, 92.8 g (10 equivalents) of acrylic acid chloride was added dropwise to the above-described reaction solution over 3 hours in an ice bath to obtain a reaction mixture. Next, the reaction mixture was stirred at room temperature for 3 hours. Next, disappearance of a signal derived from the raw materials in the reaction mixture was checked through $^1$H-NMR, and then the solvent was distilled off from the reaction mixture under reduced pressure to obtain a reaction product. Next, the above-described reaction product was dried with magnesium sulfate and was subjected to celite filtration, and the solvent was distilled off from the filtrate under reduced pressure to obtain a product. Next, the above-described product was purified through column chromatography (ethyl acetate/methanol=4:1) to obtain a compound (I) (yield of 40%) as a white solid at normal temperature. The compound (I) is a compound represented by Formula (1-1).

<Synthesis of Compound (II)>

The compound (II) was synthesized according to the following scheme.

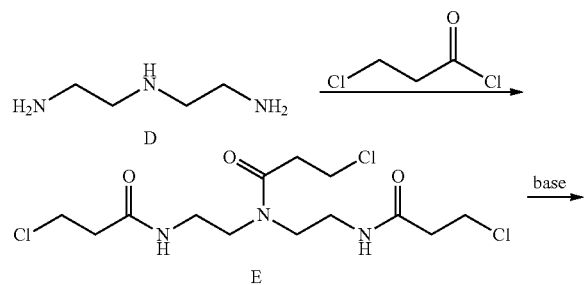

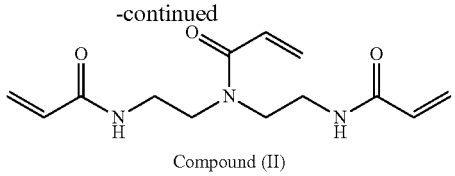

Compound (II)

10.3 g of diethylenetriamine (D) (manufactured by Tokyo Chemical Industry Co., Ltd.), 35.35 g (3.5 equivalents) of triethylamine, and 1 L of acetonitrile were added to a 2 L three-neck flask equipped with a stirrer to obtain a reaction solution. Next, 41.57 g (3.3 equivalents) of 3-chloropropionic acid chloride was added dropwise to the obtained reaction solution over 2 hours in an ice bath to obtain a reaction mixture. Next, the obtained reaction mixture was stirred at room temperature for 1 hour. Next, disappearance of a signal derived from the raw materials in the reaction mixture was checked through $^1$H-NMR, and then the solvent was distilled off from the reaction mixture under reduced pressure to obtain a reaction product. Next, the obtained product was subjected to celite filtration to obtain a filtrate. Next, the solvent was distilled off from the filtrate under reduced pressure to obtain a product. Next, the obtained product was purified through column chromatography (ethyl acetate/methanol=6:1) to obtain a white intermediate (E) (yield of 63%) at normal temperature.

Next, 72 mL (360 mmol) of an acetonitrile solution of the intermediate (E) and a 5 N NaOH aqueous solution (manufactured by Aldrich) was added to a 500 mL three-neck flask equipped with a stirrer to obtain a reaction solution. Next, the reaction solution was stirred for 5 hours at room temperature. After the completion of the reaction was checked through high performance liquid chromatography (HPLC), the reaction solution was transferred to a separatory funnel and the aqueous phase was removed to obtain an organic phase. Next, 30 mg of 2,2,6,6-tetramethylpiperidine-1-oxyl was added to the organic phase as a polymerization inhibitor and the solvent was distilled off from the organic phase under reduced pressure to obtain a product. Next, 100 mL of acetonitrile was added to the obtained product, and the organic phase was dried with potassium carbonate. After the drying, inorganic salt was filtered using 100 mL of acetonitrile, and the solvent was distilled off under reduced pressure until the amount of the contents became half. After distilling off the solvent, seed crystals were added to the obtained product, and the mixture was stirred for 12 hours for crystallization. After the crystallization, filtration was carried out and the obtained solid matter was dried to obtain a compound (II) (23.9 g (yield of 90%)) as a white solid at normal temperature. The compound (II) is a compound represented by Formula (2-1).

<Synthesis of Compound (III)>

The compound (III) was synthesized according to the following scheme.

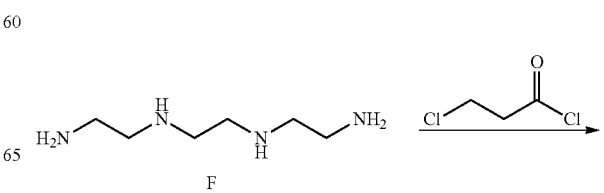

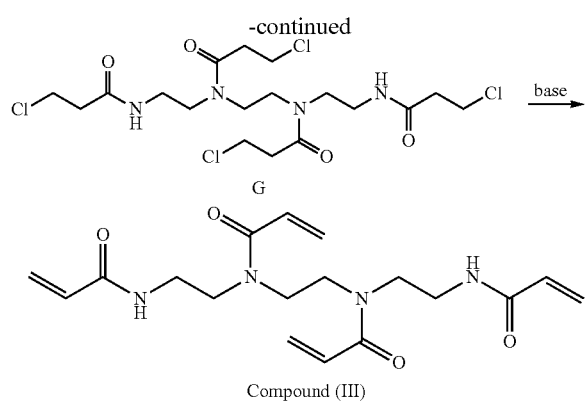

Compound (III)

14.6 g of triethylenetetramine (F) (manufactured by Aldrich), 48.48 g (4.8 equivalents) of triethylamine, and 1 L of acetonitrile were added to a 2 L three-neck flask equipped with a stirrer to obtain a reaction solution. Next, 55.42 g (4.4 equivalents) of 3-chloropropionic acid chloride was added dropwise to the obtained reaction solution over 2 hours in an ice bath to obtain a reaction mixture. Next, the reaction mixture was stirred at room temperature for 1 hour. Next, disappearance of a signal derived from the raw materials in the reaction mixture was checked through $^1$H-NMR, and then the solvent was distilled off from the reaction mixture under reduced pressure to obtain a product. Next, the obtained product was subjected to celite filtration to obtain a filtrate. Next, the solvent was distilled off from the filtrate under reduced pressure to obtain a product. Next, the obtained product was purified through column chromatography (ethyl acetate/methanol=5:1) to obtain a white intermediate (G) (yield of 55%) at normal temperature.

Next, 100 mL (500 mmol) of an acetonitrile solution of the intermediate (G) and a 5 N NaOH aqueous solution (manufactured by Wako Pure Chemical Industries, Ltd.) was added to a 500 mL three-neck flask equipped with a stirrer to stir the reaction solution for 6 hours at room temperature. Next, after the completion of the reaction was checked through HPLC, the reaction solution was transferred to a separatory funnel and the aqueous phase was removed to obtain an organic phase. Next, 30 mg of 2,2,6,6-tetramethylpiperidine-1-oxyl was added to the organic phase as a polymerization inhibitor and the solvent was distilled off from the organic phase under reduced pressure to obtain a product. Next, 100 mL of acetonitrile was added to the obtained product, and the organic phase was dried with potassium carbonate. After the drying, inorganic salt was filtered using 100 mL of acetonitrile, and the solvent was distilled off under reduced pressure until the amount of the contents became half. After distilling off the solvent, seed crystals were added to the obtained product, and the mixture was stirred for 12 hours for crystallization. After the crystallization, filtration was carried out and the obtained solid matter was dried to obtain a compound (III) (28.9 g (yield of 80%)) as a white solid at normal temperature. The compound (III) is a compound represented by Formula (2-2).

<Synthesis of Compound (IV)>

A compound (IV) was synthesized using diethylene glycol bis(3-aminopropyl) ether as raw material amine with reference to the reaction conditions of acylation disclosed in JP2012-206992A. The compound (IV) is a compound represented by Formula (3-1).

<Synthesis of Compound (V)>

Dimethylaminopropyl methacrylamide (119.18 g, manufactured by Wako Pure Chemical Industries, Ltd.), acetonitrile (350 g, manufactured by Wako Pure Chemical Industries, Ltd.), and p-methoxyphenol (0.060 g, manufactured by Wako Pure Chemical Industries, Ltd.) were placed in a 1 L three-neck flask equipped with a stirring blade and a cooling pipe to prepare a reaction solution. Next, 95.32 g of 1,4-butane sultone (manufactured by Wako Pure Chemical Industries, Ltd.) was added dropwise to the reaction solution over 30 minutes while stirring the reaction solution. After the completion of the dropwise addition, the reaction solution was heated at 80° C. for 5 hours. After the completion of the reaction, the reaction solution separated into two layers was allowed to stand for 10 hours at room temperature to precipitate a white solid from the lower layer. The white solid was collected through suction filtration in a nitrogen atmosphere, and stirred and washed in 800 mL of acetone. After the washing, the white solid was collected again through suction filtration and dried to obtain compound (V) (192.15 g). The compound (V) is a compound represented by Formula (4).

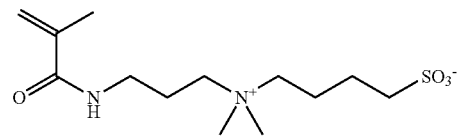

Compound (V)

Example 1

2 g of the compound (I) synthesized as described above was added to 2 g of ethanol and the mixture was stirred and dissolved to obtain a solution. Next, 1 g of 10-methacryloyloxydecyl acid phosphate (manufactured by PCM, described as "10-MDP" in Table 1) was added to and dissolved in the obtained solution. 6 g of a silica filler ("R7200" manufactured by AEROSIL, specific surface area of 150±25 m$^2$/g) was further added to the above-described solution and the mixture was stirred. 1 g of triethylene glycol dimethacrylate (described as "TEGDMA" in Table 1 and manufactured by Sigma-Aldrich Co. LLC.) and 1 g of 2,2-bis[4-[2-hydroxy-3-(methacryloyloxy) propyloxy] phenyl] propane (described as "BisGMA" in Table 1 and manufactured by Sigma-Aldrich Co. LLC.) were further added to the above-described solution and the mixture was stirred. After checking that BisGMA was dissolved, the container containing the above-described solution was placed on a hot plate at 60° C., and the solution was heated to volatilize ethanol. Finally, CAMPHORQUINONE (manufactured by Tokyo Chemical Industry Co., Ltd.) and 4-methylaminophenazone (manufactured by Sigma-Aldrich Co. LLC.) were added to the above-described solution and the mixture was stirred to obtain a root canal treatment material (S01). The content of each of the CAMPHORQUINONE and 4-methylaminophenazone in the root canal treatment material (S01) was adjusted so as to be 1 mass % with respect to the total solid content of the root canal treatment material.

Table 1 shows the composition of the root canal treatment material S01. Each numerical value in Table 1 represents the mass (unit: g) of each component. The same applies to root canal treatment materials of the following examples and comparative examples.

Example 2

A root canal treatment material (S02) was obtained through the same method as in (Example 1) except that 0.5 g of TEGDMA and 0.5 g of BisGMA were used.

Examples 3 to 8

Root canal treatment materials (S03 to S08) were obtained through the same method as in (Example 1) or (Example 2) except that the compounds (II) to (IV) were used instead of the compound (I).

Examples 9 to 16

Root canal treatment materials (S09 to S16) were obtained through the same methods as in (Examples 1 to 8) except that zirconia ("TZ-3Y-E" manufactured by TOSOH CORPORATION, a specific surface area of 16±3 $m^2/g$) was used instead of the silica filler.

Examples 17 to 24

Root canal treatment materials (S17 to S24) were obtained through the same method as in (Example 1) or (Example 2) except that a mixture of the following compounds was used instead of 2 g of the compound (I).
(S17, S18): 1 g of compound (I), 1 g of compound (II)
(S19, S20): 1 g of compound (I), 1 g of compound (III)
(S21, S22): 1 g of compound (I), 1 g of compound (IV)
(S23, S24): 1 g of compound (II), 1 g of compound (IV)

Example 25

A root canal treatment material (S25) was obtained through the same method as in (Example 1) except that a mixture of 1 g of the compound (I), 0.2 g of the compound (V), and 0.8 g of hydroxyethyl acrylamide (described as "HEAA" in Table 1) was used instead of 2 g of the compound (I).

Example 26

A root canal treatment material (S26) was obtained through the same method as in (Example 1) except that a mixture of 1 g of the compound (I) and 1 g of 2-hydroxyethyl (meth)acrylate (described as "HEMA" in Table 1) was used instead of 2 g of the compound (I).

Examples 27 to 42

Root canal treatment materials (S27 to S42) were obtained through the same methods as in (Examples 1 to 16) except that 4-(meth)acryloyloxyethyl trimellitic acid (manufactured by Designer Molecules and described as "4-MET" in Table 1) was used instead of 10-MDP.

Example 43

A root canal treatment material (S43) was obtained through the same method as in (Example 19) except that 4-MET was used instead of 10-MDP.

Comparative Example 1

A root canal treatment material (C01) was obtained through the same method as in (Example 1) except that HEMA was used instead of the compound (I).

Comparative Example 2

A root canal treatment material (C02) was obtained through the same method as in (Example 2) except that HEMA was used instead of the compound (I).

Comparative Examples 3 and 4

Root canal treatment materials (C03 and C04) were obtained through the same method as in (Example 9) or (Example 10) except that HEMA was used instead of the compound (I).

Comparative Example 5

A root canal treatment material (C05) was obtained through the same method as in (Example 1) except that methylene bisacrylamide was used instead of the compound (I).

Comparative Example 6

1 g of 10-MDP was added to 2 g of ethanol and the mixture was stirred and dissolved to obtain a solution. Next, 6 g of a silica filler was added to the obtained solution, and the mixture was stirred. 1 g of TEGDMA and 1 g of BisGMA were further added to the above-described solution and the mixture was stirred. After checking that BisGMA was dissolved, the container containing the above-described solution was placed on a hot plate at 60° C., and the solution was heated to volatilize ethanol. Finally, CAMPHORQUINONE and 4-methylaminophenazone were added to the above-described solution and the mixture was stirred to obtain a root canal treatment material (C06). The content of each of the CAMPHORQUINONE and 4-methylaminophenazone in the root canal treatment material (C06) was adjusted so as to be 1 mass % with respect to the total solid content of the root canal treatment material.

Comparative Examples 7 to 10

Root canal treatment materials (C07 to C10) were obtained through the same methods as in (Comparative Examples 1 to 4) except that 4-MET was used instead of 10-MDP.

<Evaluation of Curability>

The curability of each of the root canal treatment materials according to the examples and the comparative examples was evaluated through the following method. First, a cylindrical mold having an inner diameter of 5 mm and a height of 1 mm was filled with each of the root canal treatment materials which was then subjected to light irradiation with a light irradiator ("G-Light Prima II Plus" manufactured by GC) for 40 seconds to produce a test piece. The obtained test piece was attached to a Vicat needle tester and a Vicat needle having a mass of 100 g and a terminal diameter of 2 mm was gently lowered on the horizontal surface of the test piece. A needle mark was visually checked and evaluated according to the following criteria. The evaluation results are shown in Table 1.

A: It is completely cured without needle mark remaining.

B: It is sufficiently cured as there is almost no needle mark remaining.

C: It is cured but a slight needle mark remains.

D: It is insufficiently cured as a needle mark remains.

<Evaluation of Curability Under Moist Environment>

The curability of each of the root canal treatment materials according to the examples and the comparative examples was evaluated in a moist environment through the following method. First, 15 μL of distilled water was added to 0.15 g of each of the root canal treatment materials which was then subjected to light irradiation with the light irradiator ("G-Light Prima II Plus" manufactured by GC) for 20 seconds to produce a test piece. The curability of each of the obtained test pieces was evaluated in the same manner as in <Evaluation of Curability> described above. The evaluation results are shown in Table 1.

<Evaluation of Safety>

The safety of each cured product of the root canal treatment materials according to the examples and the comparative examples was evaluated through a cytotoxicity test. First, a mold having an inner diameter of 5 mm and a height of 1 mm was filled with each of the root canal treatment materials which was then subjected to light irradiation with a light irradiator ("G-Light Prima II Plus" manufactured by GC) for 40 seconds to obtain a test piece. The obtained test piece was placed in a well of a 12-well microplate, 1 mL of phosphate-buffered physiological saline was added thereto, and the microplate was allowed to stand in a constant-temperature tank for 24 hours at 37 in a state of being covered with a lid. Thereafter, leachate was collected from each well and used as a test sample. The cytotoxicity test was carried out through a methyl thiazolyl tetrazorium (MTT) assay described below.

First, 90 μL of a medium prepared so that the number of cells became $5 \times 10^5$ cell/mL was added to each well of a 96-well microplate, and 10 μL of a solution obtained by stepwisely diluting the test sample with a medium was further added thereto. The plate was covered with a lid and allowed to stand in a constant-temperature tank for 24 hours at 37° C. to culture the cells. Next, 10 μL of an MTT reagent was added to each well and incubated at 37° C. for 4 hours under humidification conditions. 100 μL of a solution for solubilizing a generated dye was added thereto and incubated overnight at 37° C. under humidification conditions. Thereafter, the absorbance of the above-described microplate at 550 to 680 nm was measured with an enzyme-linked immunosorbent assay (ELISA) reader by setting a wavelength of longer than or equal to 650 nm as a reference wavelength. The obtained absorbance is proportional to the number of viable cells. Leachate of the root canal treatment material (C06) was used as a control, and the measurement results of each test sample were evaluated according to the following criteria. The evaluation results are shown in Table 1.

A: The absorbance is greater than that of the control.

B: The absorbance is almost the same as that of the control.

C: The absorbance is smaller than that of the control.

D: The absorbance is considerably smaller than that of the control.

<Evaluation of Adhesiveness>

The adhesiveness of each of the root canal treatment materials to a root canal portion according to the examples and the comparative examples was evaluated through the following method. A dental root portion of the anterior tooth of the lower jaw of a cattle was cut, the dental pulp was extracted, and the dentin of a root canal portion was exposed. The exposed dentin of the root canal portion was polished with #600 waterproof abrasive paper. The polished dentin of the root canal portion was dried with compressed air without oil, and perforated double-sided tape with a diameter of 4.0 mm was stuck thereto to define an adhesive surface. Thereafter, a plastic mold having a diameter of 3.6 mm and a height of 2.0 mm was fixed to an adhesion-defined surface frame, filled with each root canal treatment material, and subjected to light irradiation with a light irradiator for 20 seconds. Then, the plastic mold was removed to produce a test piece. After immersing this test piece in distilled water at 37° C. for one day, the test piece was attached to a holding device for measuring the shear adhesion strength, and the shear adhesion strength was measured using a universal tester ("AUTOGRAPH" manufactured by Shimadzu Corporation) at a cross-head speed of 0.5 mm/min. The test was conducted ten times, and the results were arithmetically averaged and evaluated according to the following criteria. The evaluation results are shown in Table 1.

A: Greater than or equal to 5 MPa

B: Greater than or equal to 3 MPa and less than 5 MPa

C: Greater than or equal to 0 MPa and less than 3 MPa

D: A test piece cannot be produced

<Evaluation of Bending Strength>

The bending strength of each cured product of the root canal treatment materials according to the examples and the comparative examples was evaluated through the following three-point bending test method. A polytetrafluoroethylene mold having a width of 2 mm, a depth of 2 mm, and a length of 25 mm was filled with each of the root canal treatment materials which was then subjected to light irradiation with a light irradiator for 20 seconds to produce a test piece. After immersing this test piece in distilled water at 37° C. for one day, a test was performed using a universal material evaluation machine ("5565" manufactured by Instron) under the conditions of a distance between lower fulcrums of 20 mm and a test speed of 0.5 mm/min to obtain a bending stress. The test results were evaluated according to the following criteria. The evaluation results are shown in Table 1.

A: Greater than or equal to 20 MPa

B: Greater than or equal to 10 MPa and less than 20 MPa

C: Greater than or equal to 0 MPa and less than 10 MPa

D: A test piece cannot be produced

TABLE 1

| (Table 1) part 1 | C01 | C02 | C03 | C04 | C05 | C06 | C07 | C08 | C09 | C10 | S01 |
|---|---|---|---|---|---|---|---|---|---|---|---|
| Compound (I) | | | | | | | | | | | 2 |
| Compound (II) | | | | | | | | | | | |
| Compound (III) | | | | | | | | | | | |
| Compound (IV) | | | | | | | | | | | |
| Compound (V) | | | | | | | | | | | |
| Methylene bisacrylamide | | | | | | 2 | | | | | |
| HEAA | | | | | | | | | | | |

TABLE 1-continued

| (Table 1) part 1 | C01 | C02 | C03 | C04 | C05 | C06 | C07 | C08 | C09 | C10 | S01 |
|---|---|---|---|---|---|---|---|---|---|---|---|
| HEMA | 2 | 2 | 2 | 2 | | | 2 | 2 | 2 | 2 | |
| 10-MDP | 1 | 1 | 1 | 1 | 1 | 1 | | | | | 1 |
| 4-MET | | | | | | | 1 | 1 | 1 | 1 | |
| TEGDMA | 1 | 0.5 | 1 | 0.5 | 1 | 2 | 1 | 0.5 | 1 | 0.5 | 1 |
| BisDMA | 1 | 0.5 | 1 | 0.5 | 1 | 2 | 1 | 0.5 | 1 | 0.5 | 1 |
| Zirconia | | | 6 | 6 | | | | | 6 | 6 | |
| Silica filler | 6 | 6 | | | 6 | 6 | 6 | 6 | | | 6 |
| Curability | C | C | C | C | D | B | C | C | C | C | A |
| Curability in moist environment | D | D | D | D | D | D | D | D | D | D | A |
| Stability | D | D | D | D | D | B | C | C | C | C | A |
| Adhesiveness | C | C | C | C | D | C | C | C | C | C | A |
| Bending strength | C | C | C | C | D | B | C | C | C | C | A |

TABLE 2

| (Table 1) part 2 | S02 | S03 | S04 | S05 | S06 | S07 | S08 | S09 | S10 | S11 | S12 |
|---|---|---|---|---|---|---|---|---|---|---|---|
| Compound (I) | 2 | | | | | | | 2 | 2 | | |
| Compound (II) | | 2 | 2 | | | | | | | 2 | 2 |
| Compound (III) | | | | 2 | 2 | | | | | | |
| Compound (IV) | | | | | | 2 | 2 | | | | |
| Compound (V) | | | | | | | | | | | |
| Methylene bisacrylamide | | | | | | | | | | | |
| HEAA | | | | | | | | | | | |
| HEMA | | | | | | | | | | | |
| 10-MDP | 1 | 1 | 1 | 1 | 1 | 1 | 1 | 1 | 1 | 1 | 1 |
| 4-MET | | | | | | | | | | | |
| TEGDMA | 0.5 | 1 | 0.5 | 1 | 0.5 | 1 | 0.5 | 1 | 0.5 | 1 | 0.5 |
| BisDMA | 0.5 | 1 | 0.5 | 1 | 0.5 | 1 | 0.5 | 1 | 0.5 | 1 | 0.5 |
| Zirconia | | | | | | | | 6 | 6 | 6 | 6 |
| Silica filler | 6 | 6 | 6 | 6 | 6 | 6 | 6 | | | | |
| Curability | A | B | C | C | C | B | C | A | A | B | C |
| Curability in moist environment | A | B | C | C | C | B | C | A | A | B | C |
| Stability | A | B | B | A | A | B | B | A | A | B | B |
| Adhesiveness | A | A | A | B | B | A | A | A | A | A | A |
| Bending strength | B | A | B | A | B | A | B | B | B | B | B |

TABLE 3

| (Table 1) part 3 | S13 | S14 | S15 | S16 | S17 | S18 | S19 | S20 | S21 | S22 | S23 |
|---|---|---|---|---|---|---|---|---|---|---|---|
| Compound (I) | | | | | 1 | 1 | 1 | 1 | 1 | 1 | |
| Compound (II) | | | | | 1 | 1 | | | | | 1 |
| Compound (III) | 2 | 2 | | | | | 1 | 1 | | | |
| Compound (IV) | | | 2 | 2 | | | | | 1 | 1 | 1 |
| Compound (V) | | | | | | | | | | | |
| Methylene bisacrylamide | | | | | | | | | | | |
| HEAA | | | | | | | | | | | |
| HEMA | | | | | | | | | | | |
| 10-MDP | 1 | 1 | 1 | 1 | 1 | 1 | 1 | 1 | 1 | 1 | 1 |
| 4-MET | | | | | | | | | | | |
| TEGDMA | 1 | 0.5 | 1 | 0.5 | 1 | 0.5 | 1 | 0.5 | 1 | 0.5 | 1 |
| BisDMA | 1 | 0.5 | 1 | 0.5 | 1 | 0.5 | 1 | 0.5 | 1 | 0.5 | 1 |
| Zirconia | 6 | 6 | 6 | 6 | | | | | | | |
| Silica filler | | | | | 6 | 6 | 6 | 6 | 6 | 6 | 6 |
| Curability | C | C | B | C | A | A | C | C | B | B | B |
| Curability in moist environment | C | C | B | C | A | A | C | C | B | B | B |
| Stability | A | A | B | B | B | B | A | A | B | B | A |
| Adhesiveness | B | B | A | A | B | B | B | B | B | B | B |
| Bending strength | B | B | B | B | A | B | B | B | A | B | A |

TABLE 4

| (Table 1) part 4 | S24 | S25 | S26 | S27 | S28 | S29 | S30 | S31 | S32 | S33 | S34 |
|---|---|---|---|---|---|---|---|---|---|---|---|
| Compound (I) | | 1 | 1 | 2 | 2 | | | | | | |
| Compound (II) | 1 | | | | | 2 | 2 | | | | |
| Compound (III) | | | | | | | | 2 | 2 | | |
| Compound (IV) | 1 | | | | | | | | | 2 | 2 |
| Compound (V) | | 0.2 | | | | | | | | | |
| Methylene bisacrylamide | | | | | | | | | | | |
| HEAA | | 0.8 | | | | | | | | | |
| HEMA | | | 1 | | | | | | | | |
| 10-MDP | 1 | 1 | 1 | | | | | | | | |
| 4-MET | | | | 1 | 1 | 1 | 1 | 1 | 1 | 1 | 1 |
| TEGDMA | 0.5 | 1 | 1 | 1 | 0.5 | 1 | 0.5 | 1 | 0.5 | 1 | 0.5 |
| BisDMA | 0.5 | 1 | 1 | 1 | 0.5 | 1 | 0.5 | 1 | 0.5 | 1 | 0.5 |
| Zirconia | | | | | | | | | | | |
| Silica filler | 6 | 6 | 6 | 6 | 6 | 6 | 6 | 6 | 6 | 6 | 6 |
| Curability | B | B | B | A | A | B | C | C | C | B | C |
| Curability in moist environment | B | B | B | A | A | B | C | C | C | B | C |
| Stability | A | A | C | A | A | B | B | A | A | B | B |
| Adhesiveness | B | A | B | A | A | A | A | B | B | A | A |
| Bending strength | B | B | C | A | B | A | B | A | B | A | B |

TABLE 5

| (Table 1) part 5 | S35 | S36 | S37 | S38 | S39 | S40 | S41 | S42 | S43 |
|---|---|---|---|---|---|---|---|---|---|
| Compound (I) | 2 | 2 | | | | | | | 1 |
| Compound (II) | | | 2 | 2 | | | | | |
| Compound (III) | | | | | 2 | 2 | | | 1 |
| Compound (IV) | | | | | | | 2 | 2 | |
| Compound (V) | | | | | | | | | |
| Methylene bisacrylamide | | | | | | | | | |
| HEAA | | | | | | | | | |
| HEMA | | | | | | | | | |
| 10-MDP | | | | | | | | | |
| 4-MET | 1 | 1 | 1 | 1 | 1 | 1 | 1 | 1 | 1 |
| TEGDMA | 1 | 0.5 | 1 | 0.5 | 1 | 0.5 | 1 | 0.5 | 1 |
| BisDMA | 1 | 0.5 | 1 | 0.5 | 1 | 0.5 | 1 | 0.5 | 1 |
| Zirconia | 6 | 6 | 6 | 6 | 6 | 6 | 6 | 6 | |
| Silica filler | | | | | | | | | 6 |
| Curability | A | A | B | C | C | C | B | C | C |
| Curability in moist environment | A | A | B | C | C | C | B | C | C |
| Stability | A | A | B | B | A | A | B | B | A |
| Adhesiveness | B | B | B | B | B | B | B | B | B |
| Bending strength | A | B | A | B | A | B | A | B | A |

As shown in Table 1 described above, it was confirmed that the root canal treatment material containing predetermined polyfunctional acrylamide had excellent curability in a moist environment. In addition, in a case where S01 is compared with S03, S05, and S07, it was also confirmed that the compound (I) corresponding to the compound represented by Formula (1) had particularly excellent curability in a moist environment.

On the other hand, in C05 in which methylene bisacrylamide as a general polyfunctional acrylamide was used, it was impossible to obtain a desired effect.

What is claimed is:

1. A root canal treatment material comprising:
   at least one compound (A) selected from the group consisting of a compound represented by Formula (1), a compound represented by Formula (2), and a compound represented by Formula (3);
   an acidic group-containing monomer (B);
   a polymerization initiator (C); and
   a filler (D),
   wherein the filler (D) is at least one selected from the group consisting of silica, zirconia, calcium silicate, and calcium hydroxide,

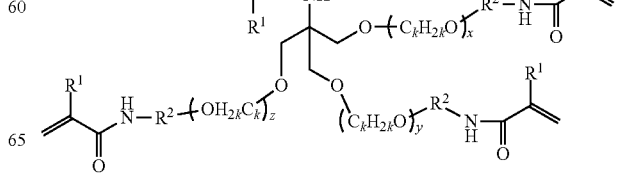

(1)

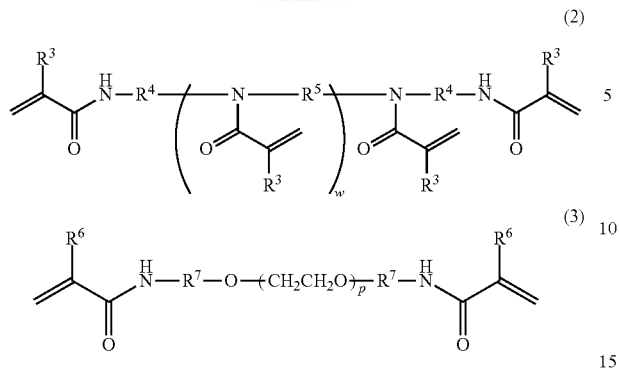

(2)

(3)

wherein in Formula (1), $R^1$'s each independently represent a hydrogen atom or a methyl group, $R^2$'s each independently represent a linear or branched alkylene group having 2 to 4 carbon atoms, provided that $R^2$ does not have a structure in which an oxygen atom and a nitrogen atom bonded to both ends of $R^2$ are bonded to the same carbon atom of $R^2$, k's each independently represent 2 or 3, x, y, and z each independently represent an integer of 0 to 6, in Formula (2), $R^3$'s each independently represent a hydrogen atom or a methyl group, $R^4$ and $R^5$ each independently represent an ethylene group or a 1,3-propylene group, and w represents an integer of 0 to 2, and in Formula (3), $R^6$'s each independently represent a hydrogen atom or a methyl group, $R^7$'s each independently represent an ethylene group, 1,2-propylene group, or a 1,3-propylene group, and p represents an integer of 2 to 6.

2. The root canal treatment material according to claim 1, wherein the compound (A) is at least one selected from the group consisting of a compound represented by Formula (1-1), a compound represented by Formula (2-1), a compound represented by Formula (2-2), and a compound represented by Formula (3-1):

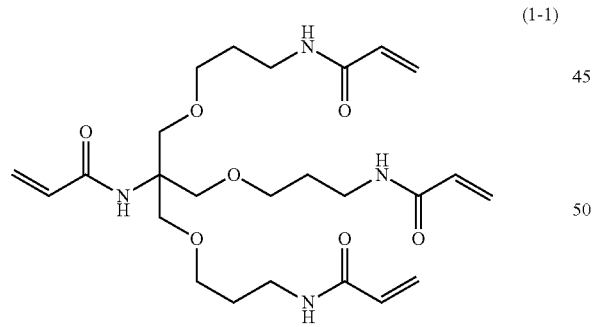

(1-1)

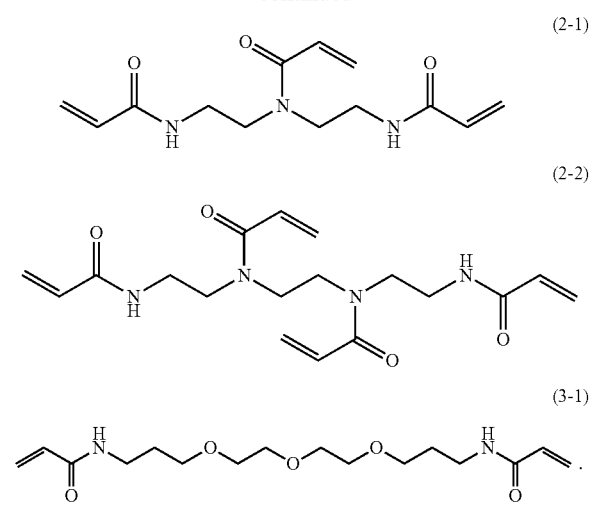

(2-1)

(2-2)

(3-1)

3. The root canal treatment material according to claim 1, wherein the acidic group-containing monomer (B) contains a compound (B1) having at least one polymerizable group and acidic group in a molecule.

4. The root canal treatment material according to claim 3, wherein the polymerizable group is a (meth)acryloyl group, and the acidic group is at least one selected from the group consisting of a carboxyl group and a phosphoric acid group.

5. A root canal treatment kit comprising:
the root canal treatment material according to claim 1.

6. The root canal treatment material according to claim 2, wherein the acidic group-containing monomer (B) contains a compound (B1) having at least one polymerizable group and acidic group in a molecule.

7. The root canal treatment material according to claim 6, wherein the polymerizable group is a (meth)acryloyl group, and the acidic group is at least one selected from the group consisting of a carboxyl group and a phosphoric acid group.

8. A root canal treatment kit comprising:
the root canal treatment material according to claim 2.

9. A root canal treatment kit comprising:
the root canal treatment material according to claim 3.

10. A root canal treatment kit comprising:
the root canal treatment material according to claim 4.

* * * * *